United States Patent [19]

Kadowaki et al.

[11] 3,992,461

[45] Nov. 16, 1976

[54] METHOD OF PRODUCING CHLOROPRENE

[75] Inventors: Takashi Kadowaki; Takao Iwasaki; Hideki Matsumura; Koichi Abe, all of Niigata, Japan

[73] Assignee: Denki Kagaku Kogyo Kabushiki Kaisha, Tokyo, Japan

[22] Filed: Aug. 21, 1969

[21] Appl. No.: 851,915

[30] Foreign Application Priority Data

Aug. 22, 1968 Japan.................................. 43-59555
Feb. 18, 1969 Japan.................................. 44-11533

[52] U.S. Cl. ............................................... 260/655
[51] Int. Cl.².......................................... C07C 21/20
[58] Field of Search................................... 260/655

[56] References Cited
UNITED STATES PATENTS

| | | | |
|---|---|---|---|
| 2,430,016 | 11/1947 | Hearne et al. | 260/655 |
| 2,999,888 | 9/1961 | Crocker et al. | 260/655 |
| 3,363,010 | 1/1968 | Schwarzenbek | 260/655 |

*Primary Examiner*—James O. Thomas, Jr.
*Assistant Examiner*—A. Siegel
*Attorney, Agent, or Firm*—Sughrue, Rothwell, Mion, Zinn and Macpeak

[57] ABSTRACT

In production of chloroprene by dehydrochlorinating 3,4-dichlorobutene-1 in the presence of an aqueous solution of alkali, the mixture of 3,4-dichlorobutene-1 and the aqueous solution of alkali is heated at 85° to 100° C to evaporate a mixture consisting mainly of the resulting chloroprene, unreacted 3,4-dichlorobutene-1 and water rapidly, the evaporated mixture is taken out from the reaction system without subjecting to a distillation and totally condensed, the condensed reaction mixture is separated into an aqueous phase and an organic phase and then the organic phase is fractionally distilled to separate chloroprene from 3,4-dichlorobutene-1. Prior to subjecting the organic phase to the fractional distillation, if the organic phase is previously subjected to a drying means and the water content in the organic phase is reduced to a proper degree, it is possible to avoid formation of polymer of the resulting chloroprene and corrosion of the distillation column.

9 Claims, 1 Drawing Figure

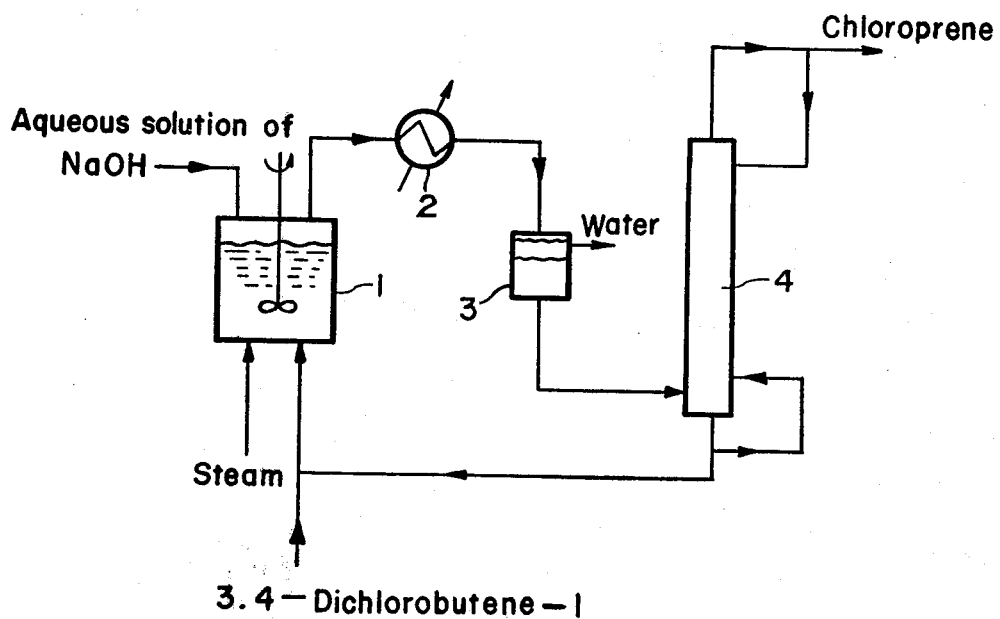

METHOD OF PRODUCING CHLOROPRENE

The present invention relates to a method of producing chloroprene by dehydrochlorinating 3,4-dichlorobutene-1.

Heretofore, two processes have been proposed in production of chloroprene by heating 3,4-dichlorobutene-1 in the presence of an aqeous solution of an alkali.

According to one process, a distilling column is provided on a reactor for dehydrochlorination and a mixture of chloroprene and water is taken out as the top fraction, but in this case the residence time of the resulting chloroprene in the reactor is substantially long and chloroprene contacts with the aqeous solution of alkali for a long time and as the result an undesirable polymer is formed in the reactor and the operation is retarded and 3,4-dichlorobutene-1 is wasted for the formation of the undesirable polymer.

The reaction rate of dehydrochlorination is rapid and according to the experiment made by the inventors, the reaction completes within 30 minutes, if the reaction is carried out at 90° C while stirring thoroughly. However, in the conventional process, wherein the reactor is provided with a distillation column and chloroprene is distilled off in an adequate reflux ratio, the average residence time is several hours.

According to the other process (U.S. Pat. No. 3,026,360; British Patent No. 985,289), a water-immiscible organic solvent which boils above the boiling point of chloroprene is used and chloroprene is taken out in a liquid phase. However in this case, a stripper required for separation of the aqueous solution of alkali from the organic phase. Furthermore, since a solvent is used, an apparatus for recovering the solvent is necessary, and further there is a problem that chloroprene is polymerized in the stripper wherein chloroprene and the aqueous solution of alkali coexist.

The object of the present invention is to suppress the formation of polymer, which retards the operation and brings about loss of 3,4-dichlorobutene-1 and to effect the dehydrochlorination in a stable condition, thereby the yield of chloroprene is increased.

The present invention consists in a method of producing chloroprene by dehydrochlorinating 3,4-dichlorobutene-1 in the presence of an aqueous solution of alkali, which comprises effecting the reaction in such a temperature range that a mixture of the resulting chloroprene, unreacted dichlorobutene and water is evaporated rapidly, taking out the said mixture in a gaseous phase from the reaction system, condensing the evaporated mixture totally, separating an organic phase from an aqueous phase and then subjecting the organic phase to a fractional distillation to separate chloroprene from 3,4-dichlorobutene-1.

According to the method of this invention, the evaporation rate of the mixture of the resulting chloroprene, unreacted dichlorobutene and water is larger than the rate of reaction necessary for converting dichlorobutene into chloroprene completely and therefore the formed chloroprene is immediately taken out from the reactor. Consequently, the formation of undesirable polymer, which occurs owing to the contact of chloroprene with the aqueous solution of alkali for a long time can be suppressed.

The evaporated mixture from the reactor is cooled and condensed and the resulting condensate is left to stand to separate an organic phase composed of chloroprene and 3,4-dichlorobutene-1 from an aqueous phase and the organic phase is subjected to a fractional distillation to separate chloroprene from 3,4-dichlorobutene-1.

Both chloroprene and dichlorobutene are very small in the solubility to water and therefore when the separated organic phase is distilled under reduced pressure, there is no such a problem that the condenser is blocked with ice. By the distillation under a reduced pressure chloroprene can be easily separated from 3,4-dichlorobutene-1 and the formation of polymers in the distillation column can be prevented. The degree of reduced pressure is 760 – 30 mmHg and the pressure lower than 30 mmHg is not preferable commercially.

Moreover, it is possible to withdraw 1-chlorobutadiene-1,3 of a by-product in the dehydrochlorination from a middle stage of the distillation column.

The reaction temperature is 85° C to 100° C, preferably 88° C to 96° C, which is a temperature necessary for evaporating the mixture of the resulting chloroprene, unreacted dichlorobutene and water from the reactor rapidly. The upper limit of temperature is one at which 3,4-dichlorobutene-1 evaporates together with water from the reactor without reacting.

The alkali to be used in the present invention is sodium hydroxide, potassium hydroxide, sodium carbonate, potassium carbonate, calcium hydroxide and the like and is generally used as an aqueous solution of 1 to 30% by weight, preferably 5 to 15% by weight.

The molar ratio of alkali to 3,4-dichlorobutene-1 is not less than 1, preferably 1.1 to 1.5. The "molar ratio" used herein means molar ratio of an amount of alkali fed to the reactor to an amount of 3,4-dichlorobutene-1 consumed in the reactor and the maximum value may not be particularly limited and the excess alkali may be recycled to the reaction system.

For a better understanding of the invention, reference it taken to the accompanying drawing, wherein the figure is a diagram showing an embodiment of an arrangement for carrying out the process of the present invention.

Referring to the FIGURE, 1 is a reactor, 2 a condenser, 3 a decanter and 4 is a fractional distillation column. In this drawing, 3,4-dichlorobutene-1 separated as a bottom fraction is recycled to the reactor and in the decanter 3 the aqueous phase positions the upper layer and the organic phase positions the lower layer but both the phases position reversely according to the conversion of 3,4-dichlorobutene-1.

However, it has been found that the organic phase separated in the decanter contains water corresponding to solubilities of the organic substances in the organic phase and therefore there is a danger that in the separation of chloroprene from unreacted dichlorobutene, the distillation column is corroded and an undesirable polymer is formed to block the column and the operation is retarded.

Namely, if dichlorobutene coexists with water, a metal surface is corroded at a relatively high temperature (higher than 50° C) due to a trace of hydrogen chloride and further chloroprene coexisting with water forms undesirable polymer (particularly pop corn-like polymer) owing to the catalytic function of the corroded surface and the column is liable to be blocked.

Another object of the present invention is to solve the practical problems of corrosion and block of the column in the above described method.

The inventors have found that such problems can be solved by removing water dissolved in the organic phase composed of unreacted dichlorobutene and chloroprene by means of usual drying means prior to subjecting the mixture to the fractional distillation.

As the usual drying agents, use may be made of calcium chloride, silica gel, alumina, calcium sulfate, synthetic zeolite and the like.

It has been found that the required extent of the drying varies depending upon the operation temperature in the distillation step but that, in general, if the water content remaining in the organic phase is 0.04% by weight, satisfactory result can be attained and the amount of less than 0.01% by weight can accomplish the object completely.

The following table shows the results of the corrosion test with respect to three kinds of metal. In this test, dichlorobutene containing water as shown in the table is kept at 100° C and each test piece is immersed in the dichlorobutene and left to stand for one month and then taken out and the weight of each test piece decreased is measured.

The numeral values in the table show the rate of corrosion (mm/year). From this table it can be seen that if the amount of water in dichlorobutene is larger, the corrosion is very liable to be caused.

Table

| Sample piece | Water Content % by weight | 10.0 | 0.07 | 0.05 | 0.035 | 0.0078 |
|---|---|---|---|---|---|---|
| Rolled steel for general structure | | 64.1 | 0.483 | 0.451 | 0.053 | 0.002 |
| AISI-316 | | 3.2 | 0.044 | 0.033 | 0.01 | 0.001 |
| NAR-20-20MCu *(Trade Mark) | | 1.7 | 0.002 | 0.002 | <0.001 | <0.001 |

*Acid resistant particular alloy, C: less than 0.08,Cr: 18 – 20, Ni: 20 – 22, Mo: 1.75 – 2.75,Cu: 1 – 2.5, Fe: remainder.

Usual polymerization inhibitors, such as, tert-butylcatechol, N-nitroso-N-methylaniline and the like may be added to the reactor, the distillation column and the other places where chloroprene is present, in an amount of 0.05 to 0.2% by weight based on 3,4-dichlorobutene-1. In addition, as a stabilizer, sodium nitrite may be added in an amount of 0.01 to 0.2% by weight based on the alkali solution.

The following examples are given in illustration of this invention and are not intended as limitations thereof.

EXAMPLE 1

In this example, the process was effected by using an apparatus as shown in the above described figure. 100 volume parts of stainless steel reactor provided with a stirrer was filled with 5% by weight of aqueous solution of sodium hydroxide and steam was introduced thereto to keep temperature at 90° C.

3,4-dichlorobutene-1 and 5% by weight of aqueous solution of sodium hydroxide were supplied into the reactor in a rate of 20 volume parts and 125 volume parts per hour respectively.

The bottom solution in the reactor was withdrawn to maintain the volume of reactants constant. The vapour from the reactor was totally condensed immediately in a condenser and then water was separated in a decanter. The organic phase was analyzed by a gas-chromatograph.

In this example and the following examples, tert-butylcatechol of 0.1% by weight based on 3,4-dichlorobutene-1 and an aqueous solution of sodium nitrite of 0.1% by weight based on the alkali solution were used as the polymerization inhibitor.

The yield of chloroprene based on the used dichlorobutene was 78% and the yield of chloroprene based on the consumed 3,4-dichlorobutene-1 was 98%.

The concentrations of chloroprene and 3,4-dichlorobutene-1 contained in the drain from the reactor were 0.01% by weight and 0.03% by weight respectively, which agreed with each of the solubilities to water.

The formation of the polymer was slight and even after a continuous operation, another continuous operation was effected without hindrance.

EXAMPLE 2

100 volume parts of a stainless steel reactor provided with a stirrer, was filled with 5% by weight of aqueous solution of sodium hydroxide and the reactor was heated externally and maintained at 90° C and 3,4-dichlorobutene-1 and 5% by weight of aqueous solution of sodium hydroxide were fed thereto in a rate of 40 volume part and 210 volume part per hour respectively.

The same treatment as described in Example 1 was effected and the yield of chloroprene based on the used 3,4-dichlorobutene-1 was 64% and the yield of chloroprene based on the consumed 3,4-dichlorobutene-1 was 97.5%.

EXAMPLE 3

The organic phase separated by a decanter described in Example 1 was continuously distilled under a reduced pressure system of 130 mmHg ab by means of a column having a diameter of 100 mm and a height of 3 mm and filled with Raschig ring having a diameter of 15 mm and the compositions of the bottom fraction and the top fraction were as follows:

| | Chloroprene | 1-chlorobutadiene-1,3 | 3,4-dichlorobutene-1 |
|---|---|---|---|
| Top fraction | 98.2 | 1.7 | 0.1 |
| Bottom fraction | 0.8 | 0.2 | 99.0 |

The above numeral values show % by weight. The loss due to the distillation was 1%.

COMPARATIVE EXAMPLE

The same reactor as described in Example 1 was connected with a turbogrid plate distillation column (16 plates) and 3,4-dichlorobutene-1 and 5% by weight of aqueous solution of sodium hydroxide were fed thereto in a rate of 4.2 parts by volume and 36 parts by volume per hour respectively.

The reaction temperature was 90° C and the reflux ratio was 5 to 10.

The yield of chloroprene obtained as the top fraction was 96% based on the consumed 3,4-dichlorobutene-1.

EXAMPLE 4

The example used the apparatus as shown in the attached drawing. Into the reactor were fed 20 parts by volume of 3,4-dichlorobutene-1 and 88 parts by volume of 5% by weight of aqueous solution of sodium hydroxide and the content was always kept at 100 parts by volume and the reaction mixture was heated to 95° C and then at this temperature 3,4-dichlorobutene-1 and 5% by weight of aqueous solution of sodium hydroxide were fed thereto in a rate of 20 parts by volume and 88 parts by volume per hour.

The temperature of the reaction mixture was maintaind at 95° C by introducing steam into the reactor.

The evaporated reaction mixture was delivered into the condenser and condensed totally therein. The condensate was fed into the decanter and separated into an organic phase and an aqueous phase and the organic phase was analyzed with gaschromatograph to obtain the following results.

| | |
|---|---|
| Chloroprene | 42.02% by weight |
| 1-chlorobutadiene-1,3 | 0.95% by weight |
| 3,4-dichlorobutene-1 | 56.96% by weight |
| Water | 0.07% by weight |

Then the above organic phase was added with 0.1% by weight based on the resulting mixture of tert-butyl-catechol as a polymerization inhibitor and added with water in such an amount that the total amount of water became 0.1% by weight then charged into a stainless steel distillation column having 10 plates and fractionally distilled under a reduced pressure system of 50 mmHg ab into chloroprene containing a small amount of 1-chlorobutadiene-1,3 and 3,4-dichlorobutene-1. When such a distillation was continued, pop corn-like polymer started to form in the column and 10 days after the operation, the column was substantially blocked and it was impossible to continue the operation and the column was fairly corroded.

The same organic phase was described above was passed through a column filled with synthetic zeolite and the water content in the organic phase was decreased to 0.008% by weight and the thus treated organic phase was treated under the same condition as described above. In this case, even after 30 days, the pop corn-like polymer was not grown in the column and the column was not corroded.

What is claimed is:

1. In a method of producing chloroprene by dehydrochlorinating 3,4-dichlorobutene-1 in the presence of an aqueous solution of an alkali, an improvement comprises effecting the reaction at a temperature of 85° to 100° C. to evaporate a mixture of the resulting chloroprene, unreacted 3,4-dichlorobutene-1 and water rapidly; taking out the said evaoporated reaction mixture from the reaction system without reflux to the reaction system and condensing the evaporated mixture totally; separating the condensed reaction mixture into an organic phase and an aqueous phase; and then subjecting the organic phase to a fractional distillation to separate chloroprene from 3,4-dichlorobutene-1.

2. The method as claimed in claim 1, wherein the said reaction is effected at a temperature of 88° to 96° C.

3. In a method of producing chloroprene by dehydrochlorinating 3,4-dichlorobutene-1 in the presence of an aqueous solution of an alkali, an improvement comprises effecting the reaction at a temperature of 85° to 100° C. to evaporate a mixture of the resulting chloroprene, unreacted 3,4-dichlorobutene-1 and water rapidly; taking out the said evaporated reaction mixture from the reaction system without reflux to the reaction system and condensing the evaporated mixture totally; separating the condensed reaction mixture into an organic phase and an aqueous phase; removing water contained in the organic phase to not more than 0.04% by weight; and then subjecting the thus treated organic phase to a fractional distillation to separate chloroprene from 3,4-dichlorobutene-1.

4. The method as claimed in claim 3, wherein the said reaction is effected at a temperature of 88° to 96° C.

5. The method as claimed in claim 3, wherein the separated organic phase is passed through a column filled with a drying agent.

6. The method as claimed in claim 5, wherein the said drying agent is a member selected from the group consisting of calcium chloride, silica gel, alumina, calcium sulfate and synthetic zeolite.

7. The method of claim 1 wherein the evaporation rate for removing said chloroprene, unreacted 3,4-dichlorobutene-1 and water is larger than the rate of reaction for converting 3,4-dichlorobutene-1 into chloroprene completely whereby the formed chloroprene is immediately taken from the reactor.

8. The method of claim 1 wherein said evaporated reaction mixture contains chloroprene, 3,4-dichlorobutene-1 and water.

9. The method of claim 1, wherein the produced chloroprene is immediately evaporated from the reactor and removed from the reaction zone without returning the chloroprene back into the reactor.

* * * * *